(12) United States Patent
Liu et al.

(10) Patent No.: US 9,267,930 B2
(45) Date of Patent: Feb. 23, 2016

(54) ANTIBODY AND RECOMBINANT DERIVATIVE FOR THE DETECTION OF TRINITROTOLUENE

(71) Applicants: Jinny Lin Liu, Ellicott, MD (US); Daniel Zabetakis, Brandywine, MD (US); Ellen R. Goldman, Germantown, MD (US); George P. Anderson, Bowie, MD (US)

(72) Inventors: Jinny Lin Liu, Ellicott, MD (US); Daniel Zabetakis, Brandywine, MD (US); Ellen R. Goldman, Germantown, MD (US); George P. Anderson, Bowie, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 696 days.

(21) Appl. No.: 13/653,474

(22) Filed: Oct. 17, 2012

(65) Prior Publication Data

US 2015/0268214 A1    Sep. 24, 2015

(51) Int. Cl.
*G01N 33/22*    (2006.01)
*C07K 16/44*    (2006.01)
*G01N 33/53*    (2006.01)

(52) U.S. Cl.
CPC .............. *G01N 33/227* (2013.01); *C07K 16/44* (2013.01); *G01N 33/5308* (2013.01); *C07K 2317/622* (2013.01)

(58) Field of Classification Search
None
See application file for complete search history.

(56) References Cited

PUBLICATIONS

Portolano, Lack of Promiscuity in Autoantigen-Specific Hand L Chain Combinations as Revealed by Human H and L Chain "Roulette" the Journal of Immunology (1993) 150:880-887.*
Rudikoff et al. (PNAS USA (1982) 79:1979-1983).*

* cited by examiner

*Primary Examiner* — Galina Yakovleva
*Assistant Examiner* — Andrea S Grossman
(74) *Attorney, Agent, or Firm* — US Naval Research Laboratory; Roy Roberts (57) ABSTRACT

Described herein are new recognition elements (antibodies or functional fragments thereof) that effectively bind to trinitrotoluene (TNT). Also disclosed is a single chain fragment recognition element.

9 Claims, 5 Drawing Sheets

```
                         SEQUENCE LISTING

<160> NUMBER OF SEQ ID NOS: 3

<210> SEQ ID NO 1
<211> LENGTH: 120
<212> TYPE: PRT
<213> ORGANISM: Artificial Sequence
<220> FEATURE:
<223> OTHER INFORMATION: antibody VH domain

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Gly Ala
            20                  25                  30

Tyr Ala Trp Asn Trp Phe Arg Gln Phe Pro Gly Asn Lys Leu Glu Trp
        35                  40                  45

Met Gly Tyr Ile Thr Tyr Ser Gly Ser Thr Ala Tyr Asn Pro Ser Leu
    50                  55                  60

Lys Ser Arg Ile Ser Ile Ser Arg Asp Thr Ser Lys Asn Gln Phe Phe
65                  70                  75                  80

Leu His Leu Asn Ser Val Thr Ser Glu Asp Thr Ala Thr Tyr Tyr Cys
                85                  90                  95

Ala Arg Tyr Tyr Thr Tyr Asp Gly Ala Trp Phe Ala Tyr Trp Gly Gln
            100                 105                 110

Gly Thr Leu Val Thr Val Ser Pro
        115                 120

<210> SEQ ID NO 2
<211> LENGTH: 106
<212> TYPE: PRT
<213> ORGANISM: Artificial Sequence
<220> FEATURE:
<223> OTHER INFORMATION: antibody VL domain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Gly Val Thr Tyr Met
            20                  25                  30

His Trp Tyr Gln Gln Lys Ser Gly Thr Ser Pro Lys Arg Trp Ile His
        35                  40                  45

Asn Thr Ser Lys Leu Ala Ser Gly Val Pro Pro Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Gly Asn Pro Pro Thr
                85                  90                  95

Phe Gly Ala Gly Thr Lys Leu Glu Leu Lys
            100                 105
```

<210> SEQ ID NO 3
<211> LENGTH: 251
<212> TYPE: PRT
<213> ORGANISM: Artificial Sequence
<220> FEATURE:
<223> OTHER INFORMATION: synthetic construct

<400> SEQUENCE: 3

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Gly Ala
            20                  25                  30

Tyr Ala Trp Asn Trp Phe Arg Gln Phe Pro Gly Asn Lys Leu Glu Trp
        35                  40                  45

Met Gly Tyr Ile Thr Tyr Ser Gly Ser Thr Ala Tyr Asn Pro Ser Leu
    50                  55                  60

Lys Ser Arg Ile Ser Ile Ser Arg Asp Thr Ser Lys Asn Gln Phe Phe
65                  70                  75                  80

Leu His Leu Asn Ser Val Thr Ser Glu Asp Thr Ala Thr Tyr Tyr Cys
                85                  90                  95

Ala Arg Tyr Tyr Thr Tyr Asp Gly Ala Trp Phe Ala Tyr Trp Gly Gln
            100                 105                 110

Gly Thr Leu Val Thr Val Ser Pro Ala Ala Ala Gly Ser Gly Gly Gly
        115                 120                 125

Ser Gly Gly Gly Gly Ser Gly Gly Gly Ser Gly Gly Gly Gly Gly
    130                 135                 140

Ser Gln Ile Val Leu Thr Gln Ser Pro Ala Ile Met Ser Ala Ser Pro
145                 150                 155                 160

Gly Glu Lys Val Thr Met Thr Cys Ser Ala Ser Ser Gly Val Thr Tyr
                165                 170                 175

Met His Trp Tyr Gln Gln Lys Ser Gly Thr Ser Pro Lys Arg Trp Ile
            180                 185                 190

His Asn Thr Ser Lys Leu Ala Ser Gly Val Pro Pro Arg Phe Ser Gly
        195                 200                 205

Ser Gly Ser Gly Thr Ser Tyr Ser Leu Thr Ile Ser Ser Met Glu Ala
    210                 215                 220

Glu Asp Ala Ala Thr Tyr Tyr Cys Gln Gln Trp Asn Gly Asn Pro Pro
225                 230                 235                 240

Thr Phe Gly Ala Gly Thr Lys Leu Glu Leu Lys
                245                 250
```

ANTIBODY AND RECOMBINANT DERIVATIVE FOR THE DETECTION OF TRINITROTOLUENE

BACKGROUND

Antibodies can serve as recognition elements for detection of specific targets for use in medical diagnostics and sensors of various types. The capability of such tests and devices depends on the specificity and affinity of the antibody which is responsible for the core function of the assay.

A monoclonal antibody of the IgG class includes four proteins connected by disulfide bonds (two copies each of the heavy and light chains). The recognition elements that carry out the binding functions of the antibody are located in two specific domains that are part of the heavy and light chain respectively and known as the $V_H$ and $V_L$ domains. Other aspects relating to antibodies are known to those of ordinary skill in the art and may be found in, e.g., U.S. Pat. No. 8,182,811, incorporated herein by reference.

Single chain antibodies (scFv), which comprise $V_H$ and $V_L$ domains joined by a linker, can provide an alternative to whole antibodies, in that scFv can be readily expressed in *E. coli* bacteria rather than requiring more complex mammalian cell culture, and furthermore scFv are readily tailored through genetic manipulation. In contrast, the production of monoclonal antibodies necessitates expensive hybridoma cell culture and careful storage.

Trinitrotoluene (TNT) is a desirable target for sensor development for both terrorism prevention and environmental remediation, since the compound is common component in explosives formulations. Although commercial antibodies exist for detection of TNT, a need exists for antibodies with superior binding characteristics will allow for improvements in TNT detection.

BRIEF SUMMARY

In one embodiment, an isolated antibody or functional fragment thereof includes SEQ ID No: 1,

DVQLQESGPGLVKPSQSLSLTCTVTGYSITGAYAWNWFRQFPGNKLEWM

GYITYSGSTAYNPSLKSRISISRDTSKNQFFLHLNSVTSEDTATYYCAR

YYTYDGAWFAYWGQGTLVTVSP.

In another embodiment, an isolated polypeptide includes a sequence with at least 85% sequence identity to SEQ ID No: 1

BRIEF DESCRIPTION OF THE DRAWINGS

FIG. 1A shows the data in terms of absolute signal intensity, while FIG. 1B shows percent uninhibited signal versus TNT concentration.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The terms "antibody" or "recognition element" are used interchangeably herein to refer to an immunoglobulin molecule that specifically binds to, or is immunologically reactive with, a particular antigen or epitope, and includes both polyclonal and monoclonal antibodies. The term "antibody" includes genetically engineered or otherwise modified forms of immunoglobulins, such as intrabodies, peptibodies, chimeric antibodies, fully human antibodies, humanized antibodies, meditope-enabled antibodies and heteroconjugate antibodies (e.g., bispecific antibodies, diabodies, triabodies, tetrabodies, tandem di-scFv, tandem tri-scFv). The term "functional fragment" includes antigen binding fragments of antibodies including, but not limited to, antigen binding (Fab) fragment, F(ab')$_2$ fragments, Fab' fragments, Fv fragments, recombinant IgG (rIgG) fragments, single chain variable fragments (scFv) and single domain antibodies (e.g., sdAb, sdFv, nanobody) fragments.

As used herein, a single chain variable fragment (scFv) refers to a construct wherein a $V_H$ domain and a $V_L$ domain are linked by a peptide linker which allows the two domains to associate to form an antigen-binding site.

DESCRIPTION

A new anti-TNT monoclonal antibody (mAb), termed 2G5B5, was developed. The variable regions were isolated and cloned for DNA sequencing. As described in more detail below, it was found that either the $V_H$ domain alone or a scFv incorporating the $V_H$ domain could serve as a recognition element for TNT with a higher affinity compared to existing antibodies. Such antibodies and functional fragments thereof are expected to be of use in detection assays and sensors.

The sequence of V$_H$ of the 2G5B5 antibody (SEQ ID No: 1) is:

DVQLQESGPGLVKPSQSLSLTCTVTGYSITGAYAWNWFRQFPGNKLEWM
GYITYSGSTAYNPSLKSRISISRDTSKNQFFLHLNSVTSEDTATYYCAR
YYTYDGAWFAYWGQGTLVTVSP.

The sequence of V$_L$ of the 2G5B5 antibody (SEQ ID No: 2) is:

QIVLTQSPAIMSASPGEKVTMTCSASSGVTYMHWYQQKSGTSPKRWIHN
TSKLASGVPPRFSGSGSGTSYSLTISSMEAEDAATYYCQQWNGNPPTFG
AGTKLELK.

A single-chain variable fragment (scFv) was created as a fusion protein from these two domains, joined with linker, and having the following sequence (SEQ ID No: 3):

DVQLQESGPGLVKPSQSLSLTCTVTGYSITGAYAWNWFRQFPGNKLEWM
GYITYSGSTAYNPSLKSRISISRDTSKNQFFLHLNSVTSEDTATYYCAR
YYTYDGAWFAYWGQGTLVTVSPAAAGSGSGGGSSGGGSSGGGSGASGSS
QIVLTQSPAIMSASPGEKVTMTCSASSGVTYMHWYQQKSGTSPKRWIHN
TSKLASGVPPRFSGSGSGTSYSLTISSMEAEDAATYYCQQWNGNPPTFG
AGTKLELK.

The proteins were expressed in *E. coli* using conventional techniques and purified using fast protein liquid chromatography (FPLC). The scFv typically yielded about 1 to 2 mg per liter of culture. The V$_H$ yielded approximately 0.25 mg/L. The mV$_H$ protein (a mutant variant of V$_H$ described below) yielded ~0.5 mg/L.

Competitive Immunoassays.

A competitive immunoassay format is routinely used for the detection of small molecules, such as TNT. In this type of assay, the recognition element is able to bind to either a surface immobilized target-analog or to the free target in solution. When the target is absent, antibody binds only to the target-analog and maximum signal is observed. As free target is added, the recognition element can either bind to the immobilized target-analog or to the free target and the measured signal decreases as more free target is present in the sample.

Competitive immunoassays were performed as follows. Bovine serum albumin (BSA) or amino-dextran were attached to the surfaces of different microsphere beads (polystyrene or magnetic beads) using two-step EDC chemistry. The TNT analog 1,3,5-trinitrobenzene (TNB) was attached to the beads by incubating with with 0.1% TNB sulfonyl chloride, then washing. Antibodies and fragments thereof were bioinylated using conventional techniques, and the biotinylated (Bt) proteins quantified by UV-Vis optical density at 280 nm.

The assay used three components: the TNB-coated microspheres, the biotin-recognition element, and sample. To develop the standard curve, a protocol typically proceeded as follows. The TNT or nitro compound was diluted into PBSTB (PBS with 0.5% Tween 20 and 1 mg/ml BSA) in a well of a polypropylene round bottom 96 well microtiter plate. The initial concentration of TNT was 10 µg/ml. The TNT was then serially diluted into other wells of the plate by factors of 10, to give the following concentrations: 10,000, 1,000, 100, 10, 1, 0.1, 0.01, and 0.001 ng/mL of TNT. To each well 5.5 µl of the TNB coated microspheres (numbering about 100-200 microspheres) was added. Then a Bt-antibody was added at the same concentration to each well, with the optimal concentration was determined empirically. After 30 minutes equilibration and two washes with PBST, streptavidin-phycoerythrin (5 µg/mL) was added to each well and incubated for 30 minutes. The plate was washed once with PBST, resuspended with 75 µL and then the assay was evaluated by either the Luminex 100 (Luminex; Austin, Tex.) for polystyrene beads or the MAGPIX (Luminex) for the magnetic beads.

Figure 1:
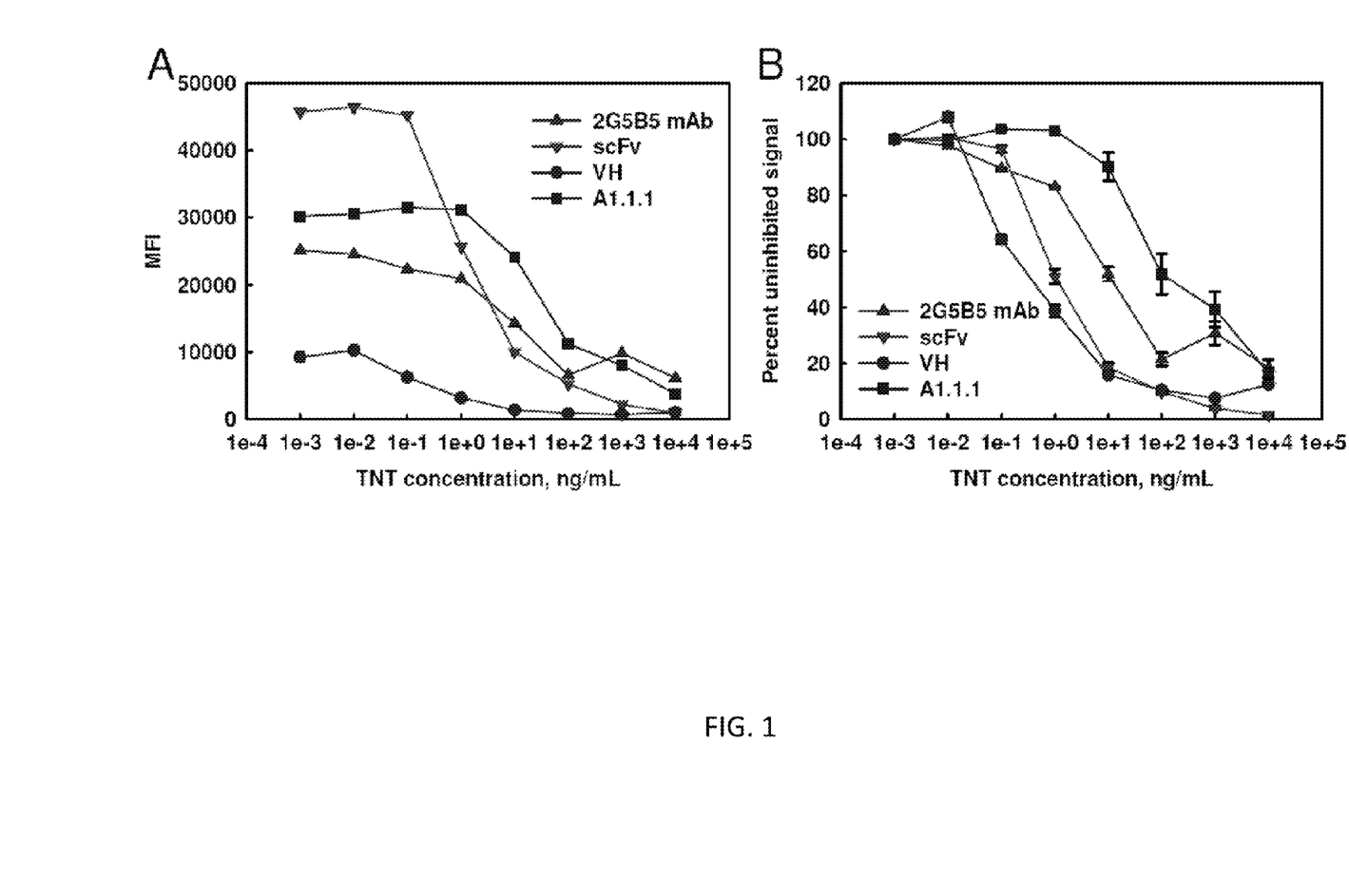
FIG. 1 shows a competitive assay for TNT detection.

Results for a competitive assay for TNT detection using the mAb, scFv, and VH are shown in FIG. 1. The data is presented in terms of absolute signal intensity in FIG. 1A, while FIG. 1B shows percent uninhibited signal versus TNT concentration. Error bars represent the standard error between duplicate bead sets. The VH appeared to provide the best limits of detection, however it also had the lowest absolute signal and the largest variability. The scFv also provided better limits of detection than the mAb 2G5B5, but unlike the VH, it also provided a strong absolute signal and small variability. Under these conditions, the 2G5B5 and its derivatives all performed better than the commercially available anti-TNT antibody, A1.1.1. It is important to note that the limits of detection are dependent on the concentration of antibody reagent used in the experiments. When using optimal concentrations, the scFv provided the best detection.

Figure 2:
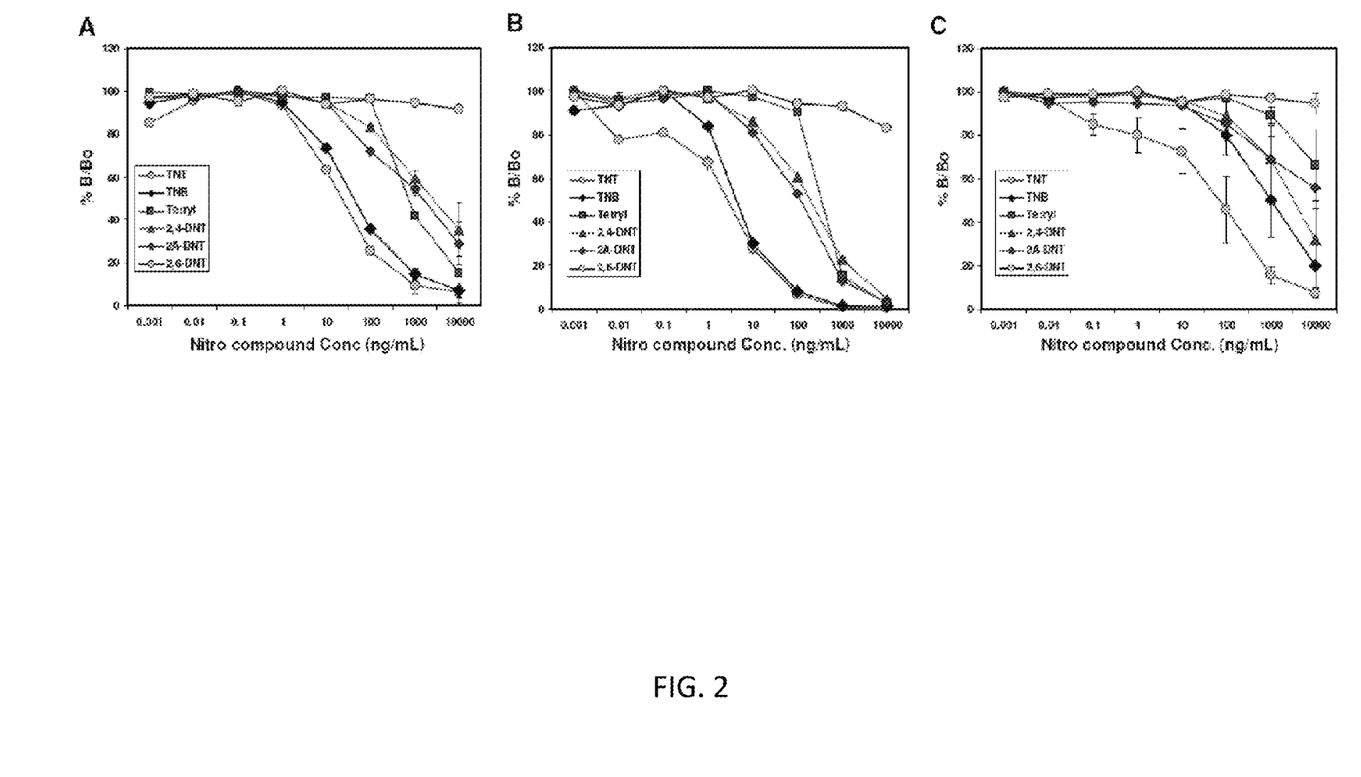
FIG. 2 shows cross reactivities of mAb2 2G5B5 (FIG. 2A), scFv 2G5B5 (FIG. 2B), and mAb A1.1.1 (FIG. 2C), plotted as percent uninhibited signal versus concentration of the nitro compound.

The cross reactivity of the mAb 2G5B5 and its derived scFv with a panel of nitro compounds and TNT-derivatives was also tested using the same competitive assay format. FIG. 2 shows cross reactivities of mAb2 2G5B5 (FIG. 2A), scFv 2G5B5 (FIG. 2B), and mAb A1.1.1 (FIG. 2C), plotted as percent uninhibited signal versus concentration of the nitro compound. The binding profiles of 2G5B5 and the scFv are essentially identical; the A1.1.1 profile shows different affinity for several of the nitro-compounds. The largest difference is in their ability to detect TNB, with the 2G5B5 showing much higher affinity than the A1.1.1. This was not unexpected, as the 2G5B5 mAb was originally made using a TNB molecule attached to Keyhole limpet hemocyanin (KLH) as the immunogen. Other mAbs developed using this or other TNB derivatives for immunization also showed substantial cross-reactivity with TNB.

Binding Kinetics.

Surface plasmon resonance (SPR) measurements were performed using the ProteON XPR36 (Bio-Rad; Hercules, Calif.). For testing the binding kinetics of the anti-TNT monoclonal and fragments a GLC chip was first coated with bovine serum albumin (BSA) and ovalbumin (Ova) on three lanes each. For immobilization, the BSA was diluted in 10 mM acetate buffer pH 5.0 and the Ova in pH 4.0. The proteins were immobilized to the chip following the standard EDC coupling chemistry provided by the manufacturer. The RU (resonance units) obtained was much higher for the BSA spots (2905, 2750, and 1390) than for the Ova spots (206, 117, and 59) due to the fact that the pI for Ova is 3.6, which immobilizes poorly since it is electrostatically repelled from the surface. After the proteins had been immobilized the chip was removed from the instrument and 100 mM borate buffered (pH 8.0) solution of TNB sulfonyl chloride 0.1% was used to saturate the remaining amines on the immobilized BSA and Ova with TNB. This resulted in three lanes with a high density of TNB and three lanes with relatively low density TNB. Experiments were performed at 25° C. The binding of the anti-TNT IgG and the various fragments were tested by flowing six concentrations of each at concentrations varying from 100 to 0 nM at 50 µL/min for 120 s over the antigen coated chip and then monitoring dissociation for 600 s. The chip was regenerated using 50 mM glycine-HCl (pH 2.5) for 36 s, prior to any additional testing. The data were analyzed with the ProteON Manager™ 2.1 software, corrected by subtraction of the zero antibody concentration column as well as interspot corrected; the binding constants were determined using the software's Bivalent analyte model or Langmuir model.

SPR was used to measure the binding of the 2G5B5 mAb, scFv, and VH to a TNB surface. Results are shown in Table 1 and FIG. 3.

TABLE 1

Binding kinetics on a TNB surface.

|  | ka (1/MS) | kd (1/S) | $KD^1$ (M) |
|---|---|---|---|
| mAb 2G5B5 | $1.7 \times 10^5$ | $2.6 \times 10^{-8}$ | $1.5 \times 10^{-13}$ |
| scFv 2G5B5 | $2.5 \times 10^5$ | $1.9 \times 10^{-4}$ | $4.8 \times 10^{-10}$ |
| VH 2G5B5[2] | $2.4 \times 10^5$ | $1.4 \times 10^{-2}$ | $7.6 \times 10^{-8}$ |

[1]Calculated from ka and kd
[2]VH 2G5B5 kinetics were determined from a high density surface, thus they do not represent true kinetic parameters.

Figure 3:
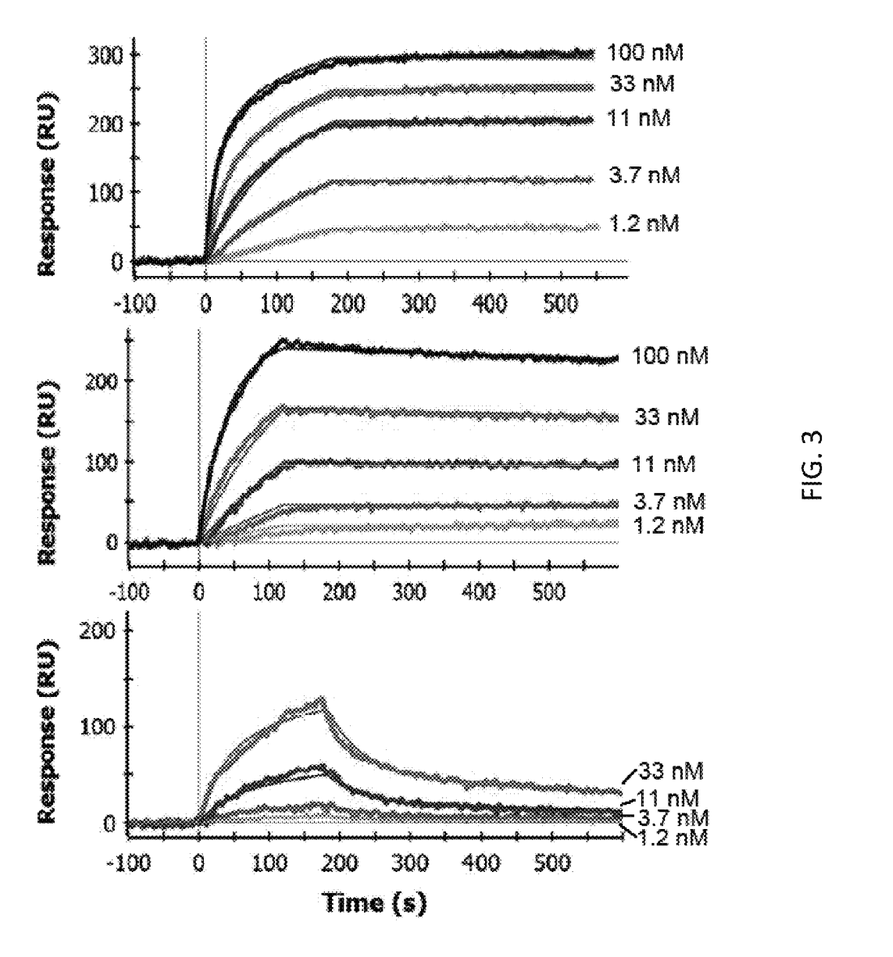
FIG. 3 shows surface plasmon resonance (SPR) measurements of binding kinetics for 2G5B5 mAb (top), scFv (middle), and VH 2G5B5 (bottom) on a 1,3,5-trinitrobenzene (TNB) surface at various concentrations.

FIG. 3 shows surface plasmon resonance (SPR) measurements of binding kinetics for 2G5B5 mAb (top), scFv (middle), and VH 2G5B5 (bottom) on a 1,3,5-trinitrobenzene (TNB) surface at various concentrations. The mAb has the slowest dissociation phase and a KD calculated to be $1.5 \times 10^{-13}$. The slow dissociation phase that this antibody can be attributed to its bivalent form. An intact mAb such as mAb 2G5B5 has two sites to bind the antigen of interest, in this case the TNT analog, TNB. If one of the antigen binding sites dissociates from the antigen, the other one can still be attached to the surface. The scFv provides good affinity to the TNB target, with a KD of $4.8 \times 10^{-10}$; however, in comparison to the whole antibody, the fragment comes off the surface more quickly. The VH demonstrated a high on rate to high density TNB on the surfaces of the chip, but not the lower TNB density surfaces used to characterize the mAb and scFv. The SPR chip was prepared with two differing densities of the TNB target. First, the chip had the proteins, BSA and ova, immobilized to three lanes, each. The chip was then removed from the instrument and the proteins reacted with TNB sulfonyl chloride. As the BSA immobilized more densely and has more available amines for the attachment of TNB the density of TNB was much higher on those surfaces, while the ova surface TNB density was much lower (<1/10). The affinity for the mAb and the scFv was determined from the lower density surface, as this limits artifacts introduced when the analyte rebinds to the ligand on the surface. The VH failed to bind to these same surfaces, but did demonstrate binding to the high density surfaces, giving an apparent affinity of $7.6 \times 10^{-8}$, but this is most likely due to rapid rebinding to the surface. This indicates that without the partner light chain, the VH fragment can bind the TNB but cannot hold on to it as well as the scFv. The VL could be directly participating in binding, as in some cases small molecules have been found to bind at the interface between VH and VL. Alternately, the VL could help the VH obtain a conformation that allows optical target binding.

The binding data can help explain the performance of the different recognition elements in the competitive assay. In conventional sandwich assays, and direct binding experiments, affinity often directly correlates with the performance of a recognition element in an assay. In a competitive format, the recognition element must be able to bind to both an immobilized surrogate and the target. Once the mAb binds to a TNB surface bivalently it does not easily come off, therefore it is unlikely to be competed as effectively by TNT free in solution. The scFv on the other hand only binds to a single TNB and thus has no preference for binding the surface bound analog relative to anlayte free in solution, other than structural variations between the analog and analyte. These results suggest that while affinity is important, the assay may achieve greater sensitivity if the affinity of the recognition element for the surrogate is not excessive.

The low signal of the VH also is understandable in the context of its high off rate from TNB; only material that stays bound to the TNB surface generates signal. In light of the SPR results, it was somewhat surprising the VH was functional at all; it appears that the TNB coated microsphere surface used in the detection experiments behaves in a similar manner to the high density TNB SPR surface. It was unclear why the scFv consistently produces signals higher than the mAb in the competitive assays; perhaps in this case a higher density of the smaller scFv could be accommodated on the micro sphere surface.

Circular Dichroism.

The melting points of the mAb and recombinant binding derivatives were measured by circular dichroism (CD) using a Jasco J-815 CD spectropolarimeter equipped with a PTC-423S single position peltier temperature control system. Samples (~25 µg/mL) were prepared by dialysis versus 5 mM sodium borate pH 8.0, or by dilution into the sodium borate buffer. Measurements were made in a 10 mm pathlength quartz cuvette with a stir bar, and melting point data were acquired at a single wavelength between 202 and 210 nm, at a temperature rate of 5° C./min over the range of 25° C. to 95° C.

Figure 4:
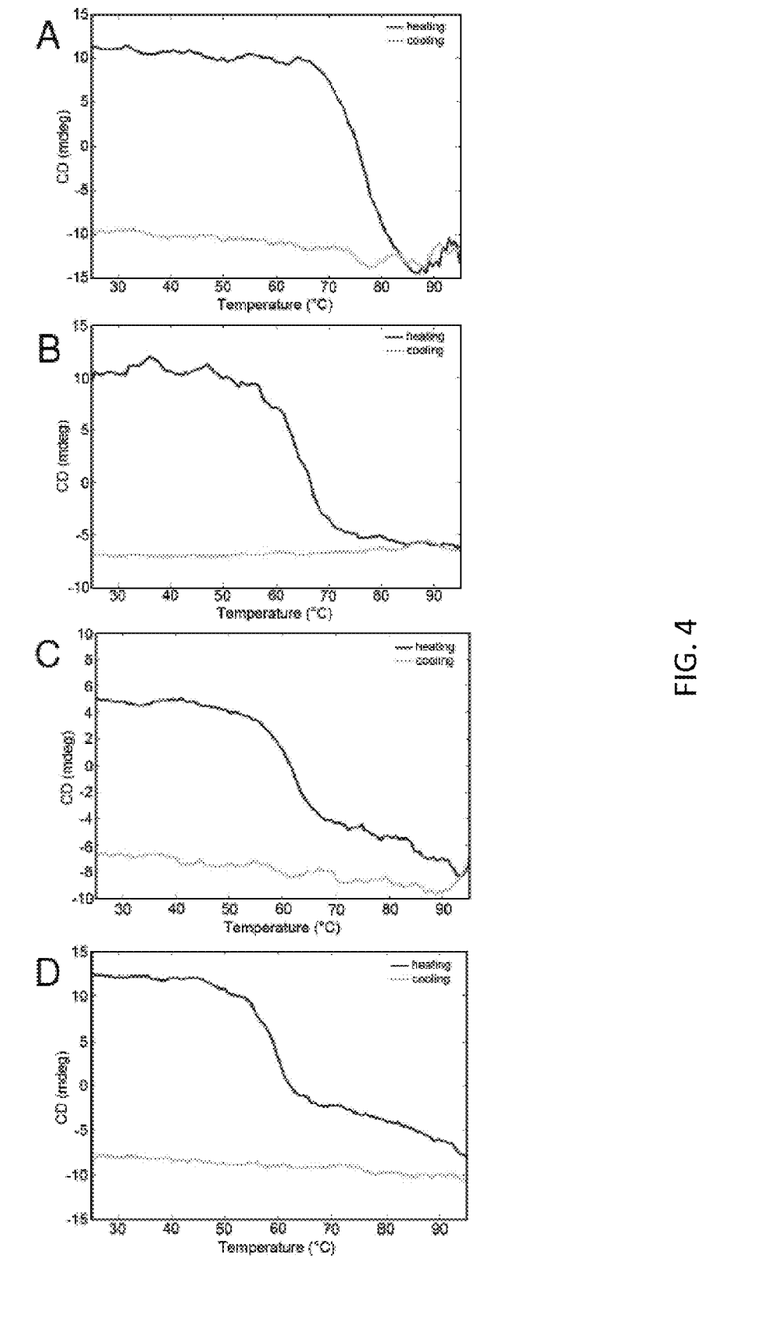
FIG. 4 shows data from the determination of melting temperatures using circular dichrosim (CD) for mAb2 2G5B5 (FIG. 4A), scFv 2G5B5 (FIG. 4B), $V_H$ 2G5B5 (FIG. 4C), and a mutant form of $V_H$ ($MV_H$) (FIG. 4D). Heating and cooling curves are shown. None of the antibodies or functional fragments thereof regained secondary structure on cooling.

CD can be used to determine melting temperatures of proteins; the melting temperature is an indication of the protein's stability. FIG. 4 shows the melting curves of the mAb, scFv, and VH. Not surprisingly, the mAb has the highest melting temperature (~75° C.) followed by the scFv (~65° C.) and then the VH (~62° C.). This is in agreement with previous observations that intact mAbs are more stable than scFv. None of these recognition elements was able to re-fold after heat denaturation, which was not surprising because antibodies and their derived fragments most often aggregate irreversibly on denaturation. It is also known that unpaired VH antibody fragments are not stable and are prone to undesired aggregation without further modification. Although the VH performed well in the competitive assay, its lack of stability makes it a less-than ideal recognition reagent.

Evaluation of Mutant VH Fragments.

Efforts were made to stabilize the VH. Four positions were mutated (N35S, Q39K, L45S, W47Y); these mutations were chosen based on sequences that are found in stable and soluble VH constructs. This mutant VH (mVH) as well as the mutant VH in a scFv format (mscFv) were produced as proteins. Although the mVH produced slightly better yields in protein preparations, it did not lead to an increase in the melting temperature, as seen in FIG. 4.

Figure 5:
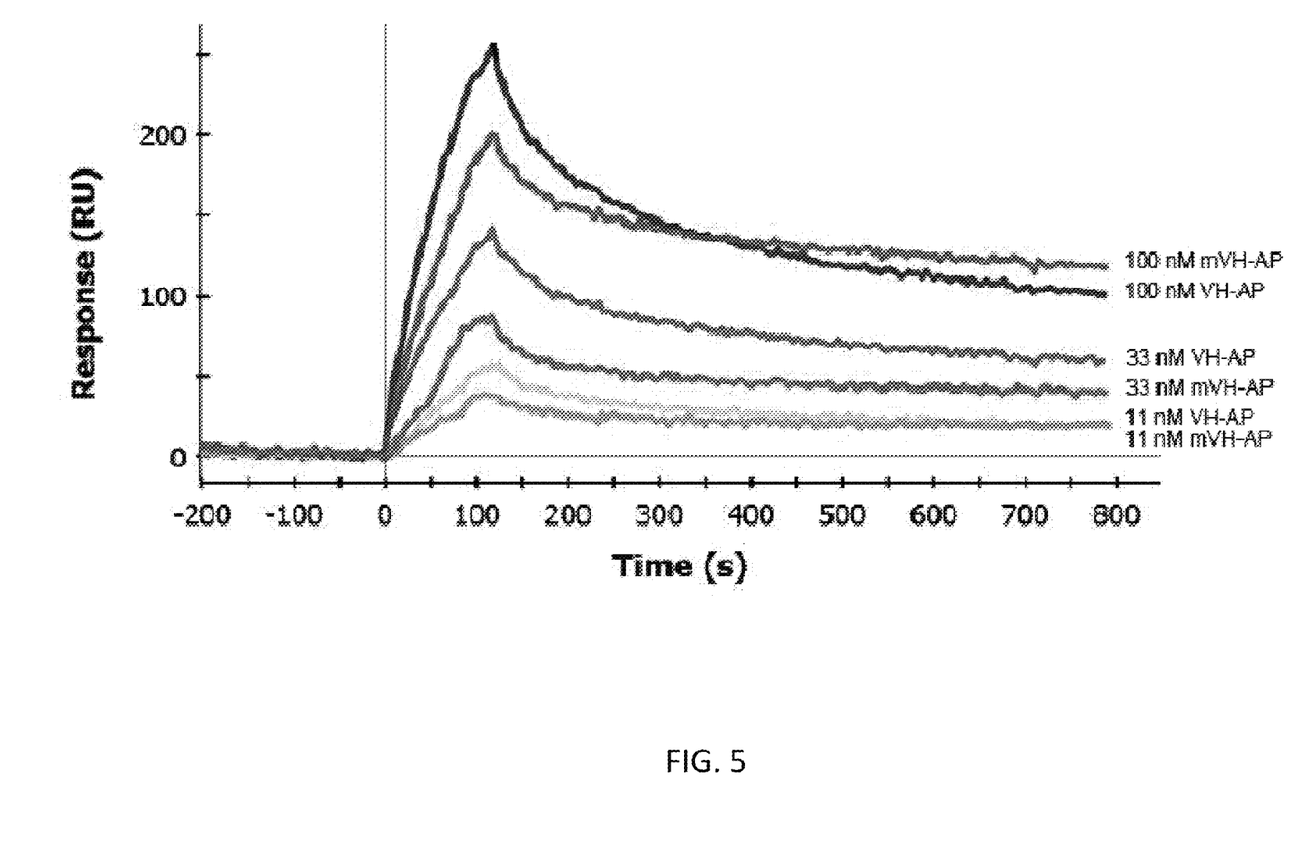
FIG. 5 shows results from SPR measurements of binding kinetics of protein fusions with alkaline phosphatase (AP) on a TNB surface for $V_H$-AP and m $V_H$-AP at various concentrations.

The VH and mVH were expressed as genetic fusions with alkaline phosphatase (AP) as the AP forms a homo dimer, resulting in constructs that possess two binding sites, similar to a mAb. Expressed as a fusion with AP, the mVH appears to have a slightly higher affinity than the VH-AP construct (FIG. 5), an increase not observed in the unfused constructs. The mVH, VH-AP, and mVH-AP were also evaluated for use in the competitive assay, but none provided any benefit over the scFv, and thus were not pursued. This result was not unexpected, since like the VH, none of these constructs bound well to the lower density TNB surface in the SPR.

Concluding Remarks.

Development of single chain antibodies for the detection of small molecules may not only alleviate the need to maintain fragile hybridoma cell lines, these recombinant molecules may actually enhance our ability to detect hazardous molecules. Although the scFv are not as stable as parental mAbs, they have more stability than other derived binding elements, such as unpaired VH.

All documents mentioned herein are hereby incorporated by reference for the purpose of disclosing and describing the particular materials and methodologies for which the document was cited. Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. An isolated antibody or functional fragment thereof that binds to trinitrotoluene, comprising a heavy chain having a sequence of SEQ ID NO:1 and a light chain having a sequence of SEQ ID NO:2.

2. The isolated antibody or functional fragment thereof according to claim 1, wherein the antibody or functional fragment thereof is a single chain variable fragment.

3. The isolated antibody or functional fragment thereof according to claim 1, wherein the isolated antibody or functional fragment thereof is a single chain antibody, wherein the combined heavy and light chain have a sequence of SEQ ID NO:3.

4. An isolated nucleic acid molecule comprising a nucleotide encoding the isolated antibody or functional fragment thereof according to claim 1.

5. A host cell in vitro transformed with the isolated nucleic acid molecule according to claim 4.

6. A method of producing an antibody or functional fragment thereof, the method comprising culturing host cells according to claim 5 under conditions for production of the antibody or functional fragment thereof.

7. The method according to claim 6, further comprising isolating and/or purifying the antibody or functional fragment thereof.

8. A method of detecting trinitrotoluene (TNT), the method comprising reacting a sample known or suspected of containing TNT with the isolated antibody or functional fragment thereof according to claim 1.

9. An apparatus configured to detect trinitrotoluene (TNT), the apparatus comprising the isolated antibody or functional fragment thereof according to claim 1.

* * * * *